United States Patent [19]

Bøttger

[11] 4,104,743
[45] Aug. 8, 1978

[54] DEVICE FOR SAFETY-HELMET WITH EAR MUFFLERS

[76] Inventor: Erik Bøttger, Kjelsåsveien 61, Oslo 4, Norway

[21] Appl. No.: 769,152

[22] Filed: Feb. 16, 1977

[30] Foreign Application Priority Data

Mar. 10, 1976 [NO] Norway .................................. 760835

[51] Int. Cl.² ............................................... A42B 1/24
[52] U.S. Cl. ....................................................... 2/423
[58] Field of Search ............................. 2/423, 209, 6; 179/156 R

[56] References Cited

U.S. PATENT DOCUMENTS

| | | | |
|---|---|---|---|
| 3,091,771 | 6/1963 | Bixby | 2/423 |
| 3,193,841 | 7/1965 | Haluska | 2/423 |
| 3,197,785 | 8/1965 | Simpson et al. | 2/423 |
| 3,461,463 | 8/1969 | Beguin | 2/423 |
| 3,845,505 | 11/1974 | Davison et al. | 2/423 X |
| 3,864,756 | 2/1975 | Desimone | 2/209 X |

Primary Examiner—Alfred R. Guest
Attorney, Agent, or Firm—Browdy and Neimark

[57] ABSTRACT

Device for a safety helmet with ear mufflers, where each ear muffler is mounted on an arm which is mounted on the helmet pivotally in a plane parallel to the longitudinal direction of the helmet. The mufflers with arms are also pivotal in a plane across the longitudinal direction of the helmet, adjustable from a noise-deadening position where the mufflers are against the ears, to an out-swung and stopped position.

6 Claims, 12 Drawing Figures

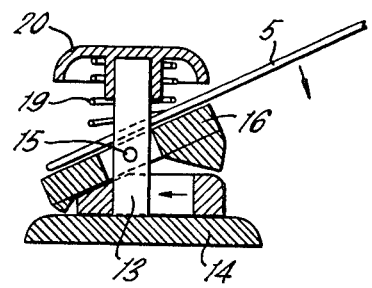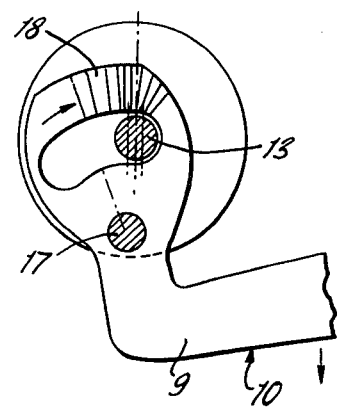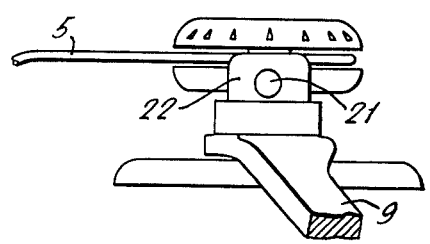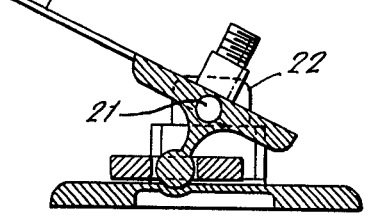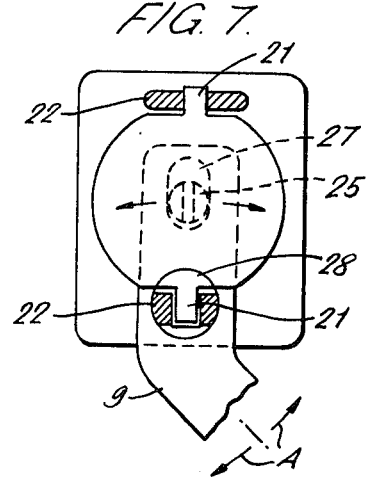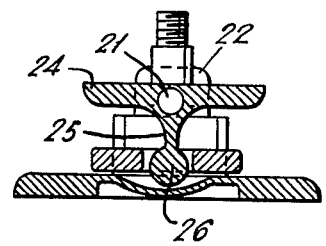

DEVICE FOR SAFETY-HELMET WITH EAR MUFFLERS

The present invention relates to a device for a safety-helmet with ear-mufflers, where each ear-muffler is mounted on an arm which again is mounted on the helmet, pivotally in a plane parallel to the longitudinal direction of the helmet.

Many work environments are noisy, and it has been established that continual noise impairs hearing in the long run. It is therefore more and more customary to equip workers in noisy work situations with ear-mufflers which to a considerable degree deaden noise. As noise often is connected with work situations where accidents are liable to occur, the mufflers are usually fastened to a safety-helmet. The ear-mufflers are located on an arm which again is pivotally mounted on the outside of the crown of the helmet, so that the ear-mufflers can be rotated forwards or backwards and thereby be removed from the ears, e.g., when the user is carrying on a conversation or comes out of the noise area.

Operation of the mufflers, in order to remove them from the ears, or to rotate them into position for use against the ears is cumbersome and requires the use of both hands. When, therefore, on the job, the ear-mufflers have to be turned around, it is necessary to drop whatever you have in your hands. For this reason, the ear-mufflers are often not used.

Safety helmets with ear-mufflers are known from U.S. Pat. No. 3,091,771, in which the mufflers are movable from one position where they lie against the ears, to an outward-swung and stopped position. The mufflers can be moved by means of a control handle placed on the outside of the helmet. The helmet is primarily intended for aviators and the like, and the ear-mufflers are not primarily intended for deadening noise, but for the transmission of radio signals, so that the latter can be taken up without being affected by noise interference. The construction is intended to suit a helmet for different head shapes and to be easy to take on and off without the ears coming in contact with the fitted-in ear-mufflers. The ear-mufflers according to the U.S. patent mentioned above, lie, namely, with a certain spring pressure against the ears in order to plug effectively, and if the ear-mufflers could not be swung out, they would be in the way when the helmet was put on and off. This previous construction is, however, very complicated and expensive, and easily damaged in other work areas, e.g., in a construction area, in mines, in road-work and the like. The helmets with ear-mufflers previously known will be expensive to produce, and price is a deciding factor for ordinary safety helmets, as these do not last long and are often exchanged.

The purpose of the present invention is to provide a device for a safety helmet with ear-mufflers where the ear-mufflers with a slight movement of the hand can easily be swung out from the ears from a noise-deadening position to a position where the bearer, e.g., can hear human voices. An additional purpose of the invention is to provide a safety helmet of the above-mentioned type which is cheap to manufacture and stands up well in use.

This is achieved according to the invention by means of a device for safety helmets with ear-mufflers, where each ear muffler is mounted on an arm which is mounted on the helmet, rotating in a plane parallel to the longitudinal direction of the helmet, and the distinctive feature of the invention is that the mufflers with arms are also pivotable in a plane across the longitudinal direction of the helmet, from a noise deadening position where the mufflers lie against the ears, to a swung-out and stopped position, and that the inner end of each muffler arm which is fastened to the helmet is controlled by the end of an operating bail which streches around the contour of the helmet, from the one fastening point for the muffler arm to the other fastening point, the bail leg of which are fastened pivotably to the two mufflers' fastening points.

In another embodiment, the muffler arm is mounted in the helmet between its ends, so that a two-armed lever with a short and a long arm is formed, where the muffler is fastened in the long arm, and that the pivotally mounted control bail acts upon the short lever arm with a cam or oblique track. The oblique track or cam is arranged on a threaded housing which is arranged at the end of each bail leg, said bail being mounted on a correspondingly threaded peg on the helmet.

Another embodiment is characterized in that the muffler arm at the end fastened to the helmet, has a wedge-shaped disc which is fastened to the crown of the helmet over a spring element, preferably a spring bail, and that this control bail which is pivotally mounted to the helmet is equipped with a cam or the like at both bail legs which interacts with this disc.

An additional embodiment is characterized in that the muffler arm is mounted in a tiltable manner on the helmet around an axis which lies across the axis for the pivotally mounted operating bail, and that from the tipping bearing of the muffler arm a peg sticks inward toward the crown of the helmet, which peg engages with the control bail, or a part connected with the latter.

The invention will as follows be explained more in detail with reference to the drawing which shows several embodiment examples of the invention.

FIGS. 3 and 4 show a primary embodiment for the mounting of a muffler arm and control bail, seen respectively from the side in cross-section, and directly from above.

FIGS. 5, 6, 7 and 8 show another embodiment for the muffler arms' and control bail's mounting on the helmet.

Figure 1:
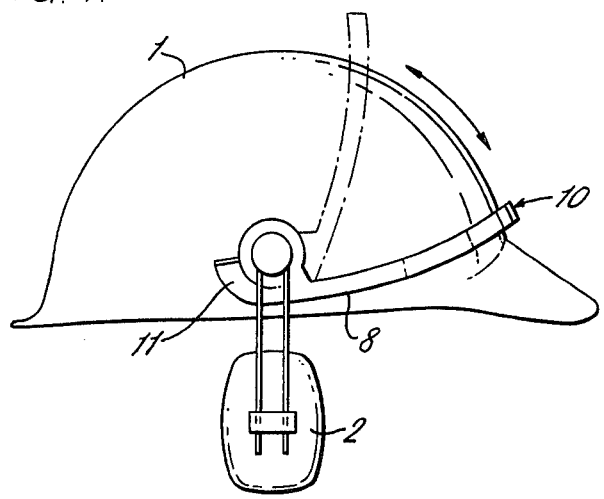
FIG. 1 shows a helmet with ear mufflers, seen from the side.
Figure 2:
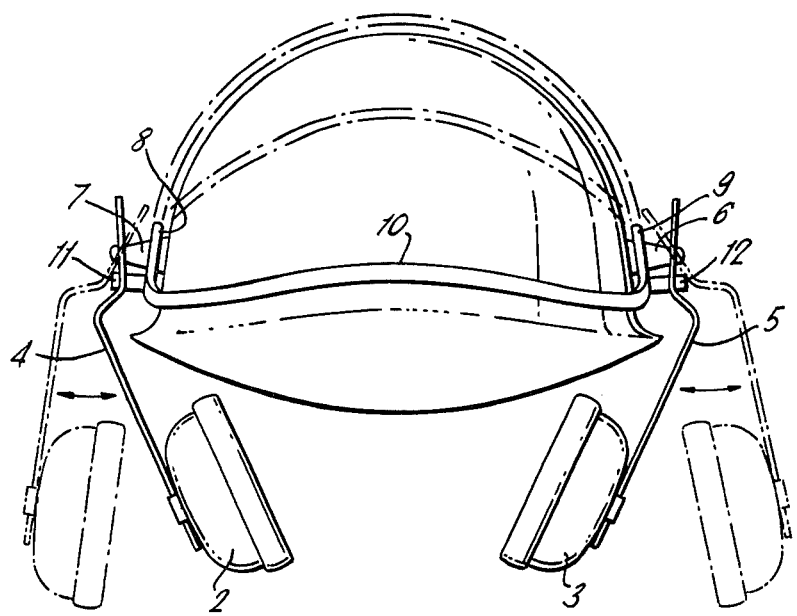
FIG. 2 shows the helmet seen from in front.

On each side of a safety-helmet 1, preferably of thermo-plastic, is mounted an ear muffler 2, 3, in such a way that they can be tilted across the longitudinal direction of the helmet. In the simple embodiment shown in FIGS. 1 and 2, the arms 4 and 5 are loosely mounted on pegs 6, 7 on the crown of the helmet. Around these pegs 6 and 7, bail legs 8 and 9 are pivotally mounted on a control bail 10. At the ends of the bail legs are placed cams 11 and 12 which lie on the under side of the inner part of the muffler arms 4 and 5. When the control bail 10 swings from the position shown by continuous lines in FIGS. 1 and 2 and upward toward the top of the helmet shown with dotted lines, the cams 11 and 12 will press the arms 4 and 5 outward, to the position shown by the dotted lines in FIG. 2 on the ear mufflers. The wearer of the helmet therefore only needs to pull the control bail upwards toward the top of the helmet with one hand, and the mufflers 2 and 3 will thereby swing out from the ears, and he will have complete hearing in both ears. With the reverse movement of the control bail 10, muffler arms 4 and 5 will turn inwards to the position shown by continuous lines in FIG. 2, where the mufflers lie with a certain spring pressure against the ears, and thus give full protection against noise.

In the embodiment shown in FIGS. 3 and 4, the muffler arm 5 is placed loosely so that it can be tilted on a peg 13 which is on a disc 14 which again is fastened to the crown 1 of the helmet. Under arm 5 a cam disc 16 is mounted in a tippable position around the pegs 15. The control bail 10 is pivotally mounted on a peg 17 which lies eccentrically in relation to the turning peg 13 for the arm 5. On the free end of the bail leg 9 on the bail 10 is placed a cam 16 which interacts with the cam disc 16. When the bail 10 is turned, the cam 18 displaces the cam disc 16 upwards and the muffler arm 5 will tilt up into the position shown in FIG. 3. A screw spring 19 is placed between muffler arm 5 and a disc-shaped nut 20 on the end of peg 13, ensures good contact between the disc 16 and the bail leg 9.

Figure 9:
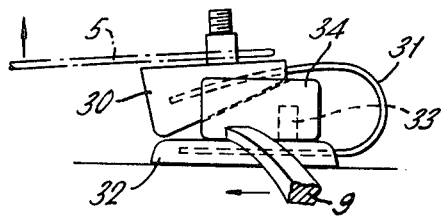
FIGS. 9 and 10 show a fourth embodiment for the mufflers arms and control bails fastening on the helmet.
Figure 10:
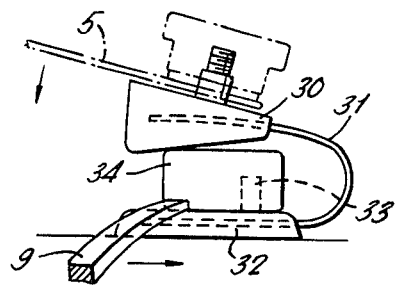

An additional embodiment for the invention is shown in FIGS. 5, 6, 7 and 8. Here a muffler arm 5 is mounted so that it can be tilted around pegs 21 which turn in bearing bushings 22, 23. The muffler arm 5 is fastened to a disc 24 which holds the pegs 21, and from the disc 24 a peg 25 sticks down toward and inward toward the crown of the helmet. The end of the peg is made ball-shaped, and it engages with an oblong track 27 in the free end of the bail leg 9, which is pivotally mounted around a peg 28 which is placed eccentrically in relation to the peg 25 (see FIG. 7). By moving bail leg 9 in the direction of the arrows 28, the peg 25 will be moved from side to side, and the muffler arm 5 will move the ear muffler in toward and away from the ear respectively. In FIGS. 9 and 10 is shown a very simple embodiment for the fastening of a muffler arm 5 to the crown of the helmet 1. To the inner end of the muffler arm 5 is fastened a bevelled disc 30 and this disc is fastened by means of a spring bail 31 to the crown of the helmet 1 and over a fastening disc 32. On the fastening disc 32 is placed a peg 33 around which the inner end of a control bail arm 9 can turn. On the inner end of the control arm is placed a cam 34 which, when the bail leg 9 is turned, will slip in against the bevelled disc 30 and press the latter up from the position which is shown in FIG. 9, to the position which is shown in FIG. 10.

Figure 11:
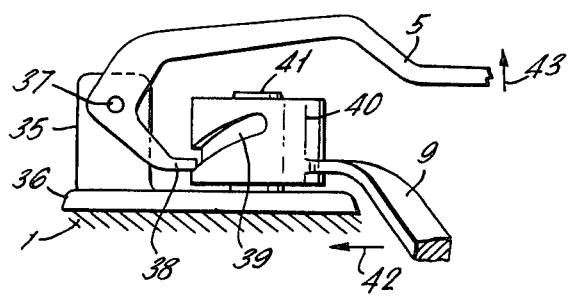
FIGS. 11 and 12 show a fifth embodiment for the same.
Figure 12:
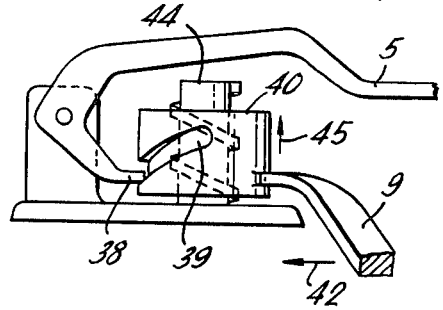

In FIGS. 11 and 12 are shown in addition an embodiment for a muffler arm's 5 fastening to the helmet crown 1. The inner end of the muffler arm 5 is fastened so that it can be tilted in the ears 35 which over a disc 36 are fastened to the crown of the helmet. An extension 38 of the arm 5 sticks out from the tilting axis 37. This extension engages with an oblique track 39 on a housing 40, which is fastened to the control bail leg 9 and mounted pivotally on a peg 41 which is again fastened in the crown of the helmet 1. When the bail leg 9 is turned in the arrow's 42 direction, the extension 38 will be pressed upwards on account of the track 39, and the muffler arm 5 will move in the direction of the arrow 43, i.e., away from the ear. In FIG. 12 is shows a modification of the construction in FIG. 11, in that the housing 40 is threaded and mounted on a threaded peg 44. When the bail leg 9 is turned, the threaded housing 40 will be pressed upward in the directon of the arrow 45, and the upward-swinging of the extension 38 because of the engaging with the track 39 will be reinforced.

All embodiments have in common that both ear mufflers 2 and 3 will be swung away from the ears through a single simple swinging-up of the control bail 10. A corresponding swinging in of the mufflers will occur when the bail 10 is swung down.

The invention is not limited to the embodiments shown and described above, but the details can be varied in a number of ways within the scope of the invention.

Having described my invention, I claim:

1. Device for a safety-helmet with ear mufflers, where each ear muffler is mounted on an arm which is mounted pivotally on the helmet, in a plane parallel to the longitudinal direction of the helmet, characterized in that the mufflers with arm are also pivotable in a plane across the longitudinal direction of the helmet, from a noise deadening position where the mufflers lie against the ears, to a swung-out and stopped position from the ears, and that the inner end of each muffler arm, which is fastened to the helmet, can be controlled by the end of a control bail, which stretches around the contour of the helmet, from the one fastening point for a muffler arm to the other fastening point, the bail legs of which are fastened so that they can be turned at the fastening points of the two muffler arms.

2. Device according to claim 1, characterized in that the inner end of the muffler arms is mounted around a horizontally, tippable disc with a knob or cam which is acted upon by the control bail.

3. Device according to claim 2, characterized in that the muffler arms are mounted in the helmet between their ends, so that a two-armed lever is formed, with a short arm and a long arm, where the muffler is fastened in the long arm, and that the pivotally mounted control bail controls the short arm by means of a cam or an oblique track.

4. Device according to claim 3, characterized in that the oblique track or the cam is put on a threaded housing which is arranged at the end of a control bail leg on a correspondingly threaded peg on the helmet.

5. Device according to claim 2, characterized in that the muffler arms carry at their end which is fastened to the helmet, a wedge-shaped disc, which is fastened to the helmet over a spring element, preferably a spring bail, and that the control bail, which is pivotally mounted to the helmet is equipped with a cam or the like interacting with this disc.

6. Device according to claim 2, characterized by the muffler arms being mounted on the helmet in a tipping position, and an axis which lies across the axis for the pivotally mounted control arm, that from the muffler arms tilt bearings, a peg sticks inward toward the helmet crown, which peg engages with the control bail legs, or a part connected with the latter.

* * * * *